(12) United States Patent
Ohue et al.

(10) Patent No.: US 11,454,632 B2
(45) Date of Patent: Sep. 27, 2022

(54) ASSAY METHOD AND ASSAY KIT FOR HEPATITIS B VIRUS S ANTIGEN

(71) Applicant: FUJIREBIO INC., Tokyo (JP)

(72) Inventors: Chiharu Ohue, Tokyo (JP); Kumiko Iida, Tokyo (JP); Katsumi Aoyagi, Tokyo (JP); Shintaro Yagi, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 346 days.

(21) Appl. No.: 16/768,419

(22) PCT Filed: Nov. 22, 2018

(86) PCT No.: PCT/JP2018/043229
§ 371 (c)(1),
(2) Date: May 29, 2020

(87) PCT Pub. No.: WO2019/107279
PCT Pub. Date: Jun. 6, 2019

(65) Prior Publication Data
US 2020/0371104 A1    Nov. 26, 2020

(30) Foreign Application Priority Data
Nov. 30, 2017 (JP) ............................. JP2017-230194

(51) Int. Cl.
*G01N 33/576* (2006.01)
*G01N 33/563* (2006.01)
*G01N 33/53* (2006.01)

(52) U.S. Cl.
CPC ....... *G01N 33/5764* (2013.01); *G01N 33/563* (2013.01); *G01N 33/5306* (2013.01); *G01N 2333/02* (2013.01)

(58) Field of Classification Search
CPC ............. G01N 33/5764; G01N 33/563; G01N 33/5306; G01N 2333/02; G01N 33/576; C07K 14/02
See application file for complete search history.

(56) References Cited

U.S. PATENT DOCUMENTS

| | | |
|---|---|---|
| 2008/0193916 A1 | 8/2008 | Maki et al. |
| 2010/0248211 A1 | 9/2010 | Matsubara et al. |
| 2015/0330982 A1 | 11/2015 | Yamagaito et al. |

FOREIGN PATENT DOCUMENTS

| | | |
|---|---|---|
| EP | 2088431 A1 | 8/2009 |
| JP | 4430677 B2 | 3/2010 |

(Continued)

OTHER PUBLICATIONS

Extended European Search Report for European Application No. 18882577.2, dated Jun. 1, 2021.

(Continued)

*Primary Examiner* — Jennifer Wecker
*Assistant Examiner* — Michael Paul Shimek
(74) *Attorney, Agent, or Firm* — Birch, Stewart, Kolasch & Birch, LLP

(57) ABSTRACT

Disclosed is a highly sensitive assay method and assay kit for HBsAg, which do not require treatment with a strong acid or alkali in the sample pretreatment, and which is less susceptible to influences by the autoantibodies. The assay method for hepatitis B virus s antigen in a sample separated from a living body includes: a pretreatment step of mixing a sample with a pretreatment reagent containing a reducing agent, to reduce hepatitis B virus s antigen; and an immunoassay step of subjecting the pretreated sample to an immunoassay of hepatitis B virus s antigen using at least one antibody or antigen-binding fragment thereof capable of antigen-antibody reaction with a reduced peptide composed (Continued)

of the amino acids at positions 98 to 179 of hepatitis B virus s antigen.

8 Claims, 1 Drawing Sheet

Specification includes a Sequence Listing.

(56) References Cited

FOREIGN PATENT DOCUMENTS

| JP | 6026564 B2 | 11/2016 |
|---|---|---|
| WO | WO 2008/053901 A1 | 5/2008 |
| WO | WO 2014/115878 A1 | 7/2014 |

OTHER PUBLICATIONS

Takeda et al., "Highly Sensitive Detection of Hepatitis B Virus Surface Antigen by Use of a Semiautomated Immune Complex Transfer Chemiluminescence Enzyme Immunoassay," Journal of Clinical Microbiology, vol. 51, No. 7, Jul. 2013, pp. 2238-2244, 7 pages total.
Waters et al., "Analysis of the antigenic epitopes of hepatitis B surface antigen involved in the induction of a protective antibody reponse," Virus Research, vol. 22, 1991, pp. 1-12, 12 pages total.
Zhu et al., "Toward the development of monoclonal antibody-based assays to provide virion-like epitopes in hepatitis B vaccine antigen," Human Vaccines & Immunotherapeutics, vol. 10, No. 4, 2014, 12 pages total.
International Search Report, issued in PCT/JP2018/043229, PCT/ISA/210, dated Feb. 26, 2019.
Written Opinion of the International Searching Authority, issued in PCT/JP2018/043229, PCT/ISA/237, dated Feb. 26, 2019.

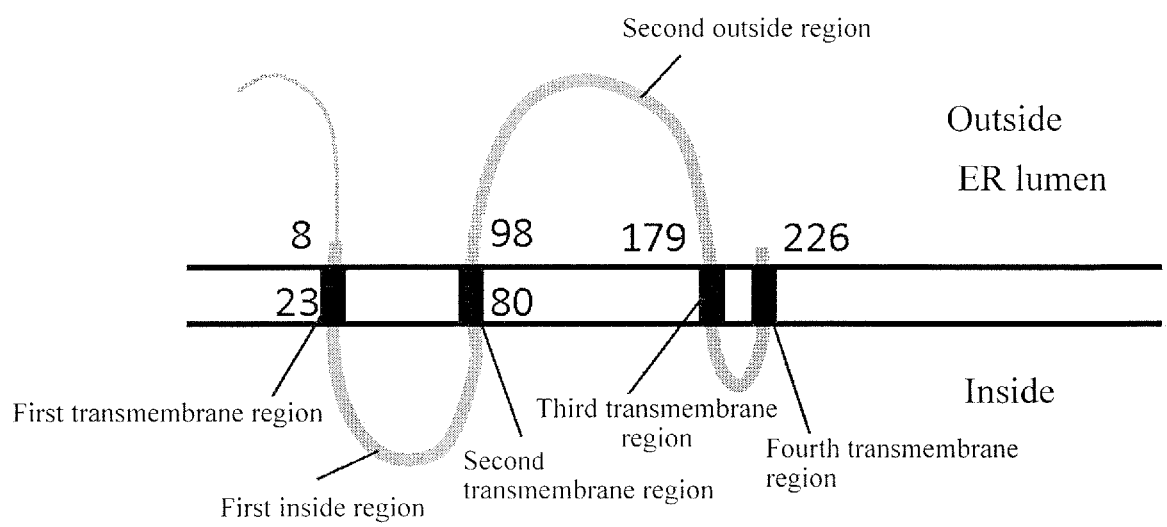

ASSAY METHOD AND ASSAY KIT FOR HEPATITIS B VIRUS S ANTIGEN

TECHNICAL FIELD

The present invention relates to an assay method and an assay kit for hepatitis B virus s antigen.

BACKGROUND ART

Hepatitis B is the most frequent disease among the liver diseases at present. It is a viral hepatitis that occurs due to infection of a human with hepatitis B virus (HBV).

The main part of hepatitis B virus is a particle called "Dane particle", which is a spherical particle with a double structure having a diameter of 42 nm. It is known that the surface of the Dane particle is covered with a surface antigen called hepatitis B virus s antigen (HBsAg), and that the particle has, in the inside thereof, a core structure having a diameter of 27 nm containing HBc antigen (core antigen), HBe antigen and a circular double-stranded DNA encoding the virus gene.

HBsAg is a major constituting coat protein on the surface of the infectious HBV particle. It is included in a lipid bilayer membrane derived from a hepatic cell, which membrane encapsulates the core particle containing the HBV-DNA. Blood of a patient infected with HBV also contains small spherical particles and tubular particles composed of HBsAg, which contain no core particle and are noninfectious. The small spherical particles are most abundantly present in the blood, and found at a ratio of about 1000 to one or several HBV particles. In the HBsAg tests that are commercially available at present, HBsAg in the form of the small spherical particle is mainly detected.

HBsAg is a transmembrane protein having a total of 226 amino acid residues and penetrating the lipid bilayer membrane four times (its amino acid sequence is shown in SEQ ID NO:1). The transmembrane structure model of HBsAg has not been completely elucidated. However, for example, Non-patent Document 1 discloses one transmembrane model (FIG. 1). According to this transmembrane model, HBsAg has four transmembrane regions. In HBsAg, the amino acid residues at positions 8 to 23 correspond to the first transmembrane region, and the amino acid residues at positions 80 to 98 correspond to the second transmembrane region. In addition, HBsAg has the first inside region of the lipid bilayer, which is composed of the amino acid residues at positions 23 to 80; the second outside (ER lumen) region which is hydrophilic and composed of the amino acid residues at positions 98 to 179; and the third transmembrane region which is hydrophobic, the second inside region, and the fourth transmembrane region, located after position 179.

In the conventional methods for analysis of HBsAg, an antibody that binds to the common antigenic determinant a of HBsAg has been typically used. The common antigenic determinant a is located on the peptide composed of the amino acid residues at positions 110 to 156 in the second outside (ER lumen) region of HBsAg, that is, in the amino acid residues at positions 98 to 179, localized on the surface of the virus particle. The common antigenic determinant a has a complex higher-order structure, and is reported to have at least four epitopes thereon (Non-patent Document 2).

Patients with acute HBV infection are positive for HBsAg in the early phase of the infection, and then become positive for HBs antibody and negative for HBsAg. In cases where blood of a patient is positive for HBs antibody, analysis of HBsAg by the methods using an antibody that binds to the common antigenic determinant a results in low measured values since binding of the antibody used for the analysis method to the HBsAg is inhibited by HBs antibodies of the patient. In view of this, the sample may be pretreated with an acidifier or an alkalizer to treat the immune complex formed by the HBs antibodies derived from the patient (autoantibodies) and the HBsAg, to avoid the influence of the autoantibodies, or the sample may be pretreated with a surfactant or the like to expose an antigen present inside the HBV particle (inside antigen, to which the autoantibodies hardly bind), and an antibody that specifically binds to the inside antigen may be used to achieve the detection (Patent Documents 1 and 2).

In patients with high HBs antibody titers, even after dissociation of the HBs antibodies (autoantibodies) from the immune complex, competitive reaction between the free autoantibodies and the antibody used for the immunoassay may still occur. Thus, there are known methods in which the free autoantibodies are further inactivated by a relatively strong acid treatment or alkali treatment (at a pH of, for example, less than 3.0 or more than 12.0) in the pretreatment step of the sample (for example, Patent Document 3).

PRIOR ART DOCUMENTS

Patent Documents

[Patent Document 1] JP 4430677 B
[Patent Document 2] EP 2088431 A1
[Patent Document 3] JP 6026564 B

Non-Patent Documents

[Non-patent Document 1] V. D. Siegler, Volker Bruss, Role of Transmembrane Domains of Hepatitis B Virus Small Surface Proteins in Subviral-Particle Biogenesis, J. Virology, 87(3) 2013, pp. 1491-1496
[Non-patent Document 2] Hiroaki Okamoto "Japanese Journal of Clinical Medicine. Molecular Hepatitis Virology—Fundamental, Clinical, and Prophylactic Aspects. Hepatitis A, B, D, and E Viruses", published on Oct. 26 (1995), pp. 212-222

SUMMARY OF THE INVENTION

Problems to be Solved by the Invention

However, in the method in which the inside antigen of the HBV particle is exposed by a surfactant treatment followed by detection of only the inside antigen, false negativity may occur depending on the HBV strain. Therefore, combination with detection of the outside antigen is necessary (Patent Document 2).

Further, in the method in which inactivation of the autoantibodies is carried out with a strong acid or alkali in the pretreatment of the sample, there are problems in, for example, that a laborious technique becomes complicated because of requirement of a neutralization step, and that the salt produced by the neutralization reaction may affect the result.

An object of the present invention is to provide a highly sensitive assay method and assay kit for HBsAg, which do not require treatment with a strong acid or alkali in the sample pretreatment, and which is less susceptible to the autoantibodies.

Means for Solving the Problems

As a result of intensive study, the present inventors discovered that the object of the present invention can be achieved by an assay of HBsAg in a sample, wherein the antigen is reduced using a reducing agent in the sample pretreatment step, and wherein, in the subsequent immunoassay, an antibody capable of reaction with a reduced peptide composed of the amino acids at positions 98 to 179 of hepatitis B virus s antigen is used.

More specifically, the present invention is as follows.
(1) An assay method for hepatitis B virus s antigen in a sample separated from a living body, the method comprising:
   a pretreatment step of mixing the sample with a pretreatment reagent containing a reducing agent, to reduce hepatitis B virus s antigen; and
   an immunoassay step of subjecting the pretreated sample to an immunoassay of hepatitis B virus s antigen using at least one antibody or antigen-binding fragment thereof capable of antigen-antibody reaction with a reduced peptide composed of the amino acids at positions 98 to 179 of the amino acid sequence of SEQ ID NO:1 in hepatitis B virus s antigen.
(2) The method according to (1), wherein
   the reducing agent is at least one reducing agent selected from the group consisting of 2-(diethylamino)ethanethiol hydrochloride (DEAET), tris(2-carboxyethyl)phosphine hydrochloride (TCEP), dithiothreitol (DTT), 2-mercaptoethanol (ME), cysteamine, and tributylphosphine (TBP); and
   the final concentration of the reducing agent in the pretreatment step is 0.5 to 100 mM.
(3) The method according to (1) or (2), wherein the antibody is capable of antigen-antibody reaction with a reduced peptide composed of the amino acids at positions 111 to 170 of the amino acid sequence of SEQ ID NO:1 in hepatitis B virus s antigen.
(4) The method according to (3), wherein the antibody is capable of antigen-antibody reaction with a reduced peptide composed of the amino acids at positions 111 to 156 of the amino acid sequence of SEQ ID NO:1 in hepatitis B virus s antigen.
(5) The method according to (4), wherein the antibody is capable of antigen-antibody reaction with a reduced peptide composed of the amino acids at positions 111 to 130 of the amino acid sequence of SEQ ID NO:1 in hepatitis B virus s antigen.
(6) The method according to any one of (1) to (5), wherein the pretreatment step is carried out under conditions at a pH of 3.0 to 12.0.
(7) The method according to any one of (1) to (6), wherein the pretreatment reagent further contains a surfactant.
(8) An assay kit for hepatitis B virus s antigen, comprising:
   (i) a pretreatment reagent containing a reducing agent; and
   (ii) an immunoassay reagent containing at least one antibody or antigen-binding fragment thereof capable of antigen-antibody reaction with a reduced peptide composed of the amino acids at positions 98 to 179 of the amino acid sequence of SEQ ID NO:1 in hepatitis B virus s antigen.

Effect of the Invention

The present invention can provide a highly sensitive assay method and assay kit for HBsAg, wherein the sample pretreatment does not require an acid/alkali treatment that may lead to a decreased sensitivity, and wherein the influence by the autoantibodies can be decreased.

BRIEF DESCRIPTION OF THE DRAWINGS

FIG. 1 is a schematic diagram illustrating a transmembrane model of HBsAg.

MODE FOR CARRYING OUT THE INVENTION

<Assay Method for HBsAg>
The method of the present invention is an HBsAg assay method comprising a pretreatment step of mixing a sample, separated from a living body, with a pretreatment reagent containing a reducing agent, which method uses, in an immunoassay, at least one antibody (which may hereinafter also be referred to as "reduced outside-recognizing antibody") or antigen-binding fragment thereof (in the following description, the term "antibody" is meant to also include "antigen-binging fragment" as long as the inclusion is contextually consistent) capable of antigen-antibody reaction with a reduced peptide composed of the amino acids at positions 98 to 179 (as counted from the N-terminus; the position number of any amino acid is counted from the N-terminus) of the amino acid sequence of SEQ ID NO:1 in hepatitis B virus s antigen (HBsAg).

The HBsAg assayed by the method of the present invention is a membrane protein which is composed of 226 amino acid residues and penetrating the lipid bilayer membrane four times. For HBV, several genotypes such as genotypes A, B, C, D, E, F, and G are known. The amino acid sequence of HBsAg varies depending on the genotype. It is also known that there are a plurality of types of antigenicity of the a region. The HBsAg to be assayed by the method of the present invention is HBsAg having an amino acid sequence that exhibits such heterogeneity.

FIG. 1 illustrates a transmembrane structure model of HBsAg. The amino acid residues at positions 98 to 179 in the transmembrane structure model of HBsAg in FIG. 1 correspond to the second outside (ER lumen) region, which is hydrophilic. In the method of the present invention, the antibody used for the antigen-antibody reaction (to be described later) is an antibody whose epitope is a reduced peptide of positions 98 to 179 of HBsAg, and the region of positions 98 to 179 corresponds to the second outside region. The peptide composed of the amino acid residues at positions 98 to 179 of HBsAg is a hydrophilic peptide present in the ER lumen outside the lipid bilayer membrane of the HBV particle. Its standard amino acid sequence is the amino acid sequence of positions 98 to 179 of SEQ ID NO:1. However, the second outside region in the present description is not limited to the peptide composed of the amino acid sequence of positions 98 to 179 of SEQ ID NO:1 in HBsAg as long as the region is the second peptide present in the outside (lumen side) of the lipid bilayer as counted from the N-terminal side of HBsAg. For example, the region may be a peptide whose amino acids have different position numbers as counted from the N-terminal side, or may be a peptide having an amino acid sequence which is the same as the amino acid sequence of positions 98 to 179 of SEQ ID NO:1 except that one or more amino acids are substituted (mutated), deleted, and/or inserted at one or more sites. It should be noted that an antibody obtained by using, as an immunogen, a peptide having such an amino acid sequence other than SEQ ID NO:1, or an antigen-binding fragments thereof, is also included in the scope of the present invention as long as the antibody or the antigen-binding fragment thereof is capable of antigen-antibody reaction with a reduced peptide composed of the amino acids at positions 98 to 179 of the amino acid sequence of SEQ ID NO:1.

1. Pretreatment Step

The method of the present invention comprises a sample pretreatment step. In the present invention, the "sample" means a specimen derived from a living body and containing HBsAg, and specific examples thereof include serum, plasma, whole blood, urine, feces, oral mucosa, pharyngeal mucosa, intestinal mucosa, and biopsy specimens (such as pancreatic specimens, intestinal specimens, and liver specimens), and dilutions thereof. The sample is preferably serum or plasma. In the present invention, the "pretreatment" means a treatment which is carried out before an immunoassay step of reacting a target molecule (in the present invention, HBsAg) with a specific antibody, in order to change the structure, properties, and/or the like of the target molecule contained in the sample. In the present invention, the pretreatment is carried out by mixing the sample with a pretreatment reagent.

The pretreatment reagent contains a reducing agent. The reducing agent is not limited, and may be any reducing agent that is normally used for cleaving S—S bonds of proteins. For example, any of existing reducing agents such as 2-(di-ethylamino)ethanethiol hydrochloride (DEAET), tris(2-car-boxyethyl)phosphine hydrochloride (TCEP), dithiothreitol (DTT), 2-mercaptoethanol, cysteamine, and tributylphosphine (TBP) may be used. DTT, TCEP, or TBP may be especially preferably used because of their excellent stability in solutions. The concentration of the reducing agent is preferably 0.5 to 100 mM, more preferably 1.0 to 50 mM, still more preferably 2.0 to 20 mM in terms of the final concentration in the mixture with the sample.

By the inclusion of the reducing agent in the pretreatment reagent, S—S bonds of the HBsAg contained in the sample are cleaved, causing dissociation of the spatial structure, to form a linear structure. By this, the spatial structure of the second outside region (hereinafter also referred to as "common antigen determinant a" or "a-loop") in the transmembrane structure model of HBsAg in FIG. 1 also becomes linear. The present inventors discovered that most autoantibodies are antibodies that recognize the spatial structure of a-loop, and that they do not react with a reduced (linear) peptide of this portion (this will be mentioned later in Example 2). By treating the sample with the pretreatment reagent containing a reducing agent, reactivity between the reduced HBsAg and the autoantibodies can be decreased, so that the negative effect of the autoantibodies on the measured value of HBsAg can be decreased.

The pH in the pretreatment step (the pH of the mixture of the sample and the pretreatment reagent) is preferably 3.0 to 12.0, more preferably 5.0 to 10.0, still more preferably 6.0 to 9.0. In the present invention, by the inclusion of the reducing agent in the pretreatment reagent, the spatial structure of HBsAg can be changed to make the target molecule of the autoantibodies practically absent. Because of the absence of the target molecule, the influence of the autoantibodies on the antigen-antibody reaction can be remarkably decreased irrespective of the presence or absence of the antibody activity. Thus, unlike the conventional techniques, the antibodies do not need to be inactivated to decrease their influence on the target molecule (antigen). Therefore, the object of the present invention can be achieved even under conditions where the pH of the pretreatment reagent is relatively close to a neutral pH. In cases where the pH of the pretreatment reagent is within the range described above, the neutralization step before the antigen-antibody reaction step can be omitted, or the amount of the neutralizer can be decreased, so that the influence of, for example, generation of salt due to the neutralization step can be avoided or decreased. Further, since deactivation of the autoantibodies in the sample becomes less likely to occur, an assay of anti-HBs antibodies in the sample can be carried out at the same time as or after the assay of HBsAg.

The pretreatment reagent may contain a pH buffer. The pH buffer is not limited as long as it is a buffer suitable for the above-described pH range. The pH buffer may be any of the pH buffers normally and widely used, such as phosphate buffer, acetate buffer, Tris, Tricine, Bicine, Tris, imidazole, triethylamine, and glycylglycine.

The pretreatment reagent may contain a surfactant. The surfactant needs to be used especially in cases where an antibody capable of antigen-antibody reaction with an inside antigen (inside-recognizing antibody) is used in combination with the reduced outside-recognizing antibody in the later-described antigen-antibody reaction step since the target region inside the HBV particle needs to be exposed. As the surfactant, any of an anionic surfactant, cationic surfactant, amphoteric surfactant, and nonionic surfactant may be used. An anionic surfactant is especially preferably used. Examples of anionic surfactants that may be preferably used include sodium dodecyl sulfate (SDS), N-lauroyl sarcosine (NLS), lithium dodecyl sulfate, sodium dodecylbenzene sulfonate, and deoxycholic acid. SDS may be especially preferably used. In cases where an anionic surfactant is used, its concentration is preferably 0.1 to 12.5%, more preferably 0.25 to 10%, still more preferably 0.5 to 7.5% in terms of the concentration (by weight) during the pretreatment of the mixture with the sample.

In cases where an anionic surfactant is included as a major surfactant in the pretreatment reagent, a neutralizing solution containing one or more of a cationic surfactant, amphoteric surfactant, and nonionic surfactant may be added for decreasing the influence by the anionic surfactant carried over into the reaction system after the pretreatment.

As the surfactant included in the pretreatment reagent, a cationic surfactant may be used instead of the anionic surfactant. The cationic surfactant is preferably a cationic surfactant containing: a single-chain alkyl group having 10 or more carbon atoms; and a tertiary amine or quaternary ammonium salt; in the same molecule. Examples of such a surfactant include decyltrimethylammonium chloride, dodecyltrimethylammonium chloride, tetradecyltrimethylammonium chloride, hexadecyltrimethylammonium chloride (C6TAC), decyltrimethylammonium bromide, dodecyltrimethylammonium bromide, tetradecyltrimethylammonium bromide, hexadecyltrimethylammonium bromide (CTAB), lauryl pyridinium chloride, tetradecyl pyridinium chloride, and cetyl pyridinium chloride. The amount of the cationic surfactant added is preferably 0.1% to 15%, more preferably 0.5% to 10% in terms of the concentration after mixing with the sample.

In addition to the cationic surfactant, another surfactant such as a nonionic surfactant may be included. By the addition of the other surfactant, detection of HBsAg is possible with even higher sensitivity.

When necessary, the pretreatment reagent may contain another protein denaturant such as urea or thiourea. The concentration of the denaturant is preferably not less than 0.1 M, more preferably not less than 0.5 M and less than 4 M in terms of the concentration during the treatment. For enhancing the treatment effect, the pretreatment reagent may also contain any one of, or a combination of, monosaccharides, disaccharides, citric acid, and citric acid salts. Further, the pretreatment reagent may also contain a chelating agent such as EDTA.

The volume ratio between the sample and the pretreatment reagent to be mixed together in the pretreatment step is preferably 1:10 to 10:1, more preferably 1:5 to 5:1, still more preferably 1:3 to 3:1. In the pretreatment step, the mixing of the biological sample with the pretreatment reagent may be followed by heating. In particular, in cases where a surfactant is used for the pretreatment reagent, heating is preferably carried out for increasing its effect. The temperature during the pretreatment step may be not higher than 95° C. preferably 20 to 90° C., still more preferably 20 to 80° C., 25 to 70° C., 25 to 60° C., 30 to 50° C., or 35 to 45° C. In the pretreatment step, the treatment time can be shortened by heating under conditions at a higher temperature. On the other hand, the pretreatment step can also be carried out under room temperature conditions. In this case, the reaction time increases, but there is no requirement of a device for high-temperature heating, which is advantageous. There is no upper limit of the reaction time in the pretreatment step. The reaction time may be usually not more than 60 minutes, especially not more than 30 minutes.

2. Immunoassay Step

The mixture treated in the pretreatment step in the method of the present invention is subsequently subjected to an immunoassay step. The immunoassay step comprises (1) an antigen-antibody reaction step and (2) a detection step.

(1) Antigen-Antibody Reaction Step

In the antigen-antibody reaction step, the mixture is mixed with an antigen-antibody reaction liquid containing an antibody against HBsAg, to react the pretreated antigen with the antibody.

The antibody used in the method of the present invention is not limited as long as it is an antibody capable of recognizing a reduced (linear) peptide composed of the amino acid sequence of positions 98 to 179 of SEQ ID NO:1. Examples of the antibody may include an antibody capable of antigen-antibody reaction with a peptide having the amino acid sequence of positions 98 to 179 of SEQ ID NO:1, and an antibody capable of antigen-antibody reaction with a peptide having an amino acid sequence which is the same as the amino acid sequence of positions 98 to 179 of SEQ ID NO:1 except that one or more amino acids are substituted (mutated), deleted, and/or inserted at one or more sites (as long as the peptide is an HBsAg fragment). More specifically, examples of the antibody include antibodies capable of antigen-antibody reaction with, for example, a peptide having the amino acid sequence of positions 121 to 130, a peptide having the amino acid sequence of positions 151 to 179, a peptide having the amino acids at positions 111 to 130, a peptide having the amino acids at positions 121 to 140, or a peptide having the amino acid sequence of positions 98 to 156, of the amino acids represented by SEQ ID NO:1, or a peptide which is the same as these peptides except that part of the amino acids are substituted (all of the peptides are linear). The antibody used in the method of the present invention is not limited as long as it is an antibody capable of antigen-antibody reaction with the linear peptides described above, and may be an antibody that recognizes a structural epitope composed of a complex higher-order structure, such as the common antigenic determinant a. Some epitopes cannot be formed with a partial peptide composed only of the amino acid sequence of positions 98 to 179 of SEQ ID NO:1, and are formed with, for example, the full-length peptide composed of 226 amino acid residues, which is the full-length HBsAg. Examples of the antibody used in the present invention include an antibody reactive with the linear peptide described above, which antibody, for example, is capable of binding to a structural epitope formed with a peptide longer than the partial peptide composed only of the amino acid sequence of positions 98 to 179 of the amino acids of SEQ ID NO:1, which structural epitope is present in the region having the amino acid sequence of positions 98 to 179 of SEQ ID NO:1.

The antibody used in the method of the present invention is not limited as long as the antibody is capable of recognizing a reduced peptide having the amino acid sequence of positions 98 to 179 of SEQ ID NO:1. Examples of the antibody include polyclonal antibodies, monoclonal antibodies, recombinant antibodies, receptors, and analogs. The antibody is preferably a monoclonal antibody or an antigen-binding fragment thereof (which may be hereinafter referred to as "antibody fragment").

The antibody fragment of the monoclonal antibody is not limited as long as it is an antibody fragment capable of recognizing a reduced peptide having the amino acid sequence of positions 98 to 179 of SEQ ID NO:1. Examples of the antibody fragment include Fab, Fab', F(ab')$_2$, and Fv. These antibody fragments can be obtained by, for example, digesting the monoclonal antibody in the present invention by a conventional method using a protease (such as pepsin or papain), followed by performing purification by a conventional protein separation/purification method.

The principle of the HBsAg assay in the method of the present invention is not limited as long as it is an immunoassay. Any well-known immunoassay such as the sandwich method, the competitive method, or the immunoagglutination method may be employed. Among these, the sandwich method, wherein HBsAg is detected using a capture antibody and a detection antibody, is preferred. Examples of the sandwich method include the forward sandwich method (wherein reaction between an immobilized antibody and the antigen in the sample, and reaction between the antigen bound to the solid phase and a labeled antibody, are sequentially carried out) and the reverse sandwich method (wherein a labeled antibody is preliminarily reacted with the antigen in the sample, and the resulting antigen-antibody complex is reacted with an immobilized antibody), which are two-step methods, and the single-step method (wherein an immobilized antibody, the antigen in the sample, and a labeled antibody are reacted at the same time in one step). Any of these methods may be employed.

In the method of the present invention, an antibody capable of recognizing a reduced peptide having the amino acid sequence of positions 98 to 179 of SEQ ID NO:1 in HBsAg (reduced outside antigen-recognizing antibody) is used as at least one of the capture antibody and the detection antibody. Preferably, reduced outside antigen-recognizing antibodies are used as both of the capture antibody and the detection antibody. In cases where a reduced outside antigen-recognizing antibody is used as the capture antibody, the detection antibody may be either a reduced outside antigen-recognizing antibody or an antibody that recognizes a reduced inside antigen. The detection antibody is preferably a reduced outside antigen-recognizing antibody. In cases where a reduced outside antigen-recognizing antibody is used as the detection antibody, the capture antibody may be either a reduced outside antigen-recognizing antibody or a reduced inside antigen-recognizing antibody. The capture antibody is preferably a reduced outside antigen-recognizing antibody. In both cases, antibodies that recognize the unreduced outside antigen structure cannot be used. In cases where only one kind of antibody is used in the competitive method or the immunoagglutination method, a reduced outside antigen-recognizing antibody is used as the one kind of antibody.

In the method of the present invention, a plurality of antibodies may be used in combination as the capture antibody and/or the detection antibody as long as at least one reduced outside antigen-recognizing antibody is used as either the capture antibody or the detection antibody.

In the method of the present invention, the immunoassay step may include a contact step of bringing the sample after the pretreatment step into contact with the capture antibody and the detection antibody, and a detection step of detecting a signal from the detection antibody, which is described later. The contact step may be carried out also as the following separate steps: a first contact step of bringing the sample into contact with the capture antibody, and a second contact step of bringing the detection antibody into contact with the antigen-antibody complex formed in the first contact step.

More specifically, for example, the forward sandwich method can be carried out as follows. First, a capture antibody that binds to HBsAg is immobilized on an insoluble support such as a microplate or magnetic beads. Subsequently, in order to prevent non-specific adsorption to the capture antibody or the insoluble support, the insoluble support is blocked with an appropriate blocking agent (such as bovine serum albumin or gelatin). The sample after the pretreatment step is added, together with a primary reaction liquid, to the plate or beads on which the capture antibody is immobilized, to bring the capture antibody into contact with, and to hind the capture antibody to, HBsAg in the sample (primary reaction step). Thereafter, the antigen not bound to the capture antibody, and impurities, are washed away using an appropriate washing liquid (such as phosphate buffer containing a surfactant). Subsequently, a labeled antibody in which an enzyme such as alkaline phosphatase (ALP) is bound to an antibody that recognizes the captured HBsAg is added thereto to bind the labeled antibody to the captured antigen (secondary reaction step). This reaction allows formation of an immune complex of capture antibody-antigen-labeled antibody, on the support such as a microplate. The unbound labeled antibody is washed away with a washing liquid, and a coloring substrate or luminescent substrate for the enzyme of the labeled antibody is added, followed by reacting the enzyme with the substrate to detect a signal.

The capture antibody used in the method of the present invention is an antibody that captures HBsAg in the sample. In the above sandwich method using an insoluble support, the capture antibody is an immobilized antibody immobilized on the insoluble support. The detection antibody used in the method of the present invention is an antibody that detects HBsAg in the sample, captured by the capture antibody. In the above sandwich method using an insoluble support, the detection antibody is a labeled antibody prepared by labeling with an enzyme or the like.

In cases where reduced outside antigen-recognizing antibodies are used as both of the capture antibody and the detection antibody, the antibodies used are those which bind to different epitopes. The "different epitopes" means epitopes that are not completely the same. For example, in cases where two antibodies are the same monoclonal antibodies, or where two antibodies are antibodies completely inhibited in an epitope inhibition test, the epitopes of the two antibodies can be said to be the same. On the other hand, in cases where the epitopes of the capture antibody and the detection antibody are partially overlapping with each other, the antibodies can be used in the method of the present invention in most cases.

Examples of the enzyme for the labeling of the antibody include horseradish peroxidase (HRP), alkaline phosphatase (ALP), β-galactosidase, and luciferase. Other than enzymes, examples of the labeling substance that may be used include luminescent substances such as acridinium derivatives, fluorescent substances such as europium, and radioactive substances such as $I^{125}$. Further, a substrate or a luminescence-inducing substance may be appropriately selected according to the labeling substance.

Further, examples of the labeled antibody in the present invention include antibodies having, as a detection marker, a substance bound thereto that can be used for detection of a signal of the antigen-antibody reaction, such as hapten, low-molecular-weight peptide, or lectin. Examples of the hapten include biotin, dinitrophenyl (DNP), and FITC. For example, in cases where biotin is bound to an antibody to prepare a probe complex, avidin, which has an affinity to biotin, may be labeled with an enzyme such as ALP, a fluorescent substance such as fluorescein, or a luminescent substance such as an acridinium derivative, and reacted with the probe complex to detect a signal based on coloring, fluorescence, luminescence, or the like.

The method of labeling the antibody is not limited, and a conventionally known method may be used. Examples of the method include a method in which the antibody is directly labeled with a labeling substance such as an enzyme, a method in which the antibody and a labeling substance such as an enzyme are bound to a macromolecular compound such as dextran, and a method in which a labeled antibody is bound to a macromolecular compound such as dextran.

Examples of the antibody of the present invention include polyclonal antibodies of animals and monoclonal antibodies of mice. The method of immunization of the animals for obtaining the antibodies and the method of obtaining hybridomas producing the monoclonal antibodies can be carried out by well-known methods except that HBsAg or a partial peptide of HBsAg is used as an immunogen. For example, the methods can be carried out according to methods described in, for example, New Biochemistry Experiments Lecture (Japanese Biochemical Society (ed.)) or Immunobiochemical Approaches (Japanese Biochemical Society (ed.)). As the HBsAg for the immunization, virus particles, or HBsAg purified from virus particles, may be used. The HBsAg and the partial peptide can be obtained by, for example, expressing the antigens in *E. coli* by genetic recombination, and then purifying the expressed antigens. Alternatively, the partial peptide of HBsAg can be prepared by chemical synthesis. It can be synthesized by, for example, Fmoc solid-phase synthesis or Boc solid-phase synthesis. The synthesized peptide can be purified by a known method such as HPLC. By placing cysteine as a terminal amino acid, and using the SH group of the cysteine, the peptide may be bound to a carrier protein to provide an immunogen.

The antibody used in the present invention can be obtained by using reduced HBsAg or a peptide fragment thereof as an immunogen for immunization of an animal. Alternatively, unreduced HBsAg or a peptide fragment thereof may be used as an immunogen to obtain a plurality of kinds of antibodies, and then reduced HBsAg or a peptide fragment thereof may be used to perform screening, to obtain the antibody used in the present invention. The animal to be immunized is not limited, and may be, for example, sheep, goat, rabbit, mouse, rat, guinea pig, bird, cow, or horse. HBsAg or a peptide fragment thereof is mixed and emulsified with, for example, an equal amount of Freund's complete adjuvant or Titer-Max gold (Titer Max), and the resulting mixture is subcutaneously administered to a rabbit, or intraperitoneally administered to a mouse. Thereafter, the same immunizing operation is carried out at 1- or 2-week intervals. By collecting blood from the thus immunized animal, and preparing serum or plasma therefrom, the antibody of the present invention can be prepared.

The hybridoma in the present invention producing the monoclonal antibody in the present invention can be obtained from the animal subjected to the immunization operation described above. For example, a mouse is subjected to several times of the immunizing operation, and, two weeks thereafter, HBsAg or a peptide fragment thereof dissolved in phosphate-buffered saline (PBS) or the like is inoculated via the tail vein. Two or three days thereafter, the spleen, which contains lymphocytes producing antibodies, is aseptically removed from the mouse. By subjecting the lymphocytes to, for example, cell fusion with myeloma cells, hybridomas producing monoclonal antibodies can be established.

The cell fusion can be carried out by, for example, fusion of the lymphocytes to the myeloma cells in the presence of polyethylene glycol. As the myeloma cells, known cells having a marker such as hypoxanthine-guanine-phosphoribosyltransferase deficiency or thymidine kinase deficiency may be used. Specific examples of the myeloma cells include cells such as p3•NS-1/1•Ag4.1 and SP2/0-Ag14. The fused cells are selected by killing the unfused cells using a selection medium such as HAT medium.

Subsequently, screening is carried out based on the presence or absence of antibody production in the culture supernatant of each grown hybridoma. The screening can be carried out by measuring the production of a specific antibody against HBsAg or a peptide fragment thereof using an enzyme-linked immunosorbent assay (ELISA method) or the like. By selecting a hybridoma clone secreting the antibody of interest, and then repeating subcloning by the limiting dilution method, the clonality of the monoclonal antibody can be secured. Thus, a hybridoma producing the antibody of the present invention can be selected.

The hybridoma in the present invention can be subcultured in a known arbitrary medium such as RPMI1640. The monoclonal antibody in the present invention can be prepared by culturing this hybridoma. For example, by adding 10% fetal bovine serum to RPMI1640 medium, and performing culture in the presence of 5% $CO_2$ at 37° C., the antibody is produced in the culture supernatant. Alternatively, the hybridoma may be intraperitoneally inoculated to a mouse pretreated with pristane to allow production of the antibody in the ascites, and the ascites may be recovered therefrom 10 to 20 days thereafter. The antibody in the present invention can be purified by a known method. The purification can be carried out by, for example, a purification method using a Protein G or Protein A column, a method using an affinity column to which HBsAg is bound, or a method using an ion-exchange column.

The epitope recognized by the monoclonal antibody obtained can be determined by an enzyme-linked immunosorbent assay (ELISA method) using a recombinant antigen prepared from an HBsAg-derived sequence, or a synthetic peptide of about 10 to 20 amino acids prepared by chemical synthesis. The epitope of the monoclonal antibody produced from each hybridoma in the present invention was determined based on reactivity with peptides composed of 20 amino acid residues, which peptides were chemically synthesized based on the amino acid sequences of HBsAg of different genotypes such that the peptides overlap with each other by 10 residues.

3. Detection Step

The detection antibody after being brought into contact with HBsAg in the antigen-antibody reaction step is detected by a method suitable for the label used for the detection antibody, such as addition of a substrate of an enzyme in cases where an enzyme label is used. For example, in cases where alkaline phosphatase (ALP) is used for the labeled antibody, the method may be a system of chemiluminescent enzyme immunoassay (CLEIA) using, as an enzyme substrate, 3-(2'-spiroadamantane)-4-methoxy-4-(3'-phosphoryloxy)phenyl-1,2-dioxetane disodium salt (AMPPD).

<Assay Kit for HBsAg>

The kit of the present invention is a kit for hepatitis B virus s antigen, comprising: (1) a pretreatment reagent containing a reducing agent; and (2) an antigen-antibody reaction reagent containing at least one antibody capable of reaction with a reduced peptide composed of the amino acids at positions 98 to 179 of hepatitis B virus s antigen.

In cases where the kit contains a reagent containing the capture antibody and a reagent containing the detection antibody as separate components, the term "antigen-antibody reaction reagent" herein means one or both of the reagents, and, in cases where a reagent containing both the capture antibody and the detection antibody is used, the term means this reagent. Thus, at least one antibody capable of reaction with a reduced peptide composed of the amino acids of positions 98 to 179 of hepatitis B virus s antigen (reduced outside antigen-recognizing antibody) is used for at least one of the capture antibody and the detection antibody.

The kit of the present invention comprises the constituent reagents in a form in which they are isolated from each other, or in the form of a composition(s). More specifically, the constituent reagents may be provided in a form in which they are stored in different containers (such as a tube(s) and/or a plate(s)), or part of the constituent reagents may be provided in the form of a composition(s) (for example, in the same solution). Alternatively, the kit of the present invention may be provided in the form of a device. More specifically, the kit may be provided in a form in which all of the constituent reagents are stored in a device(s). Alternatively, part of the constituent reagents may be provided in a form in which they are stored in a device(s) while the others may be provided in a form in which they are not stored in the device(s) (for example, in a form in which they are stored in a different container(s)). In such cases, the constituent reagent(s) not stored in the device(s) may be used by injection into the device(s) in the measurement of the target substance. The kit of the present invention may also contain an HBsAg standard solution, another anti-hepatitis B virus antibody, instructions, or the like.

EXAMPLES

Example 1

Reactivity of Anti-HBsAg Monoclonal Antibodies With Reduced Antigen (1) Preparation of Unreduced/Reduced HBsAg-Immobilized Plates A commercially available native HBsAg (subtype ad, manufactured by TRINA) was diluted to 12.2 µg/mL with PBS or with PBS containing 6 M urea, to prepare antigen dilutions (urea (−), urea (+)). Dithiothreitol (DTT) was diluted with ion-exchanged water to prepare 1, 10, 50, 100, 200, 500, and 1000 mM reducing agent solutions. To each well of 96-well microwell plates (manufactured by Nunc), 90 μL of each antigen dilution was dispensed, and 10 μL of each reducing agent solution was added thereto. After leaving the plates to stand at room temperature for 60 minutes, 80 μL/well of PBS or PBS containing 6 M urea was added thereto. After leaving the plates to stand at 4° C. overnight, the plates were washed three times with PBS. After dispensing 350 μL of a blocking solution (1% BSA, 3% sucrose, substrate solution (TMB solution) was dispensed at 100 μL/well, and the plates were left to stand at room temperature for 30 minutes, followed by dispensing 2 N sulfuric acid at 100 μL/well to stop the reaction. The absorbance at 450/630 nm was measured for each well. Table 2 shows the values calculated by subtracting the absorbance of the blank (PBS alone) from the absorbance for each well.

TABLE 2

| DTT (mM) | | 0 | 0.1 | 1 | 5 | 10 | 20 | 50 | 100 |
|---|---|---|---|---|---|---|---|---|---|
| Antibody A | Urea (−) | 3.162 | 1.293 | 0.054 | 0.036 | 0.032 | 0.028 | 0.026 | 0.025 |
| | Urea (+) | 2.951 | 0.078 | 0.022 | 0.019 | 0.021 | 0.019 | 0.021 | 0.022 |
| Antibody B | Urea (−) | 0.137 | 0.150 | 0.178 | 0.206 | 0.227 | 0.229 | 0.232 | 0.231 |
| | Urea (+) | 0.150 | 0.363 | 0.763 | 1.028 | 1.101 | 1.200 | 1.330 | 1.494 |
| Antibody C | Urea (−) | 0.137 | 0.367 | 0.886 | 1.265 | 1.390 | 1.373 | 1.419 | 1.540 |
| | Urea (+) | 0.341 | 1.756 | 2.742 | 2.958 | 3.011 | 3.056 | 3.150 | 3.357 |
| Antibody D | Urea (−) | 2.535 | 3.062 | 3.205 | 3.173 | 3.186 | 3.132 | 3.191 | 3.294 |
| | Urea (+) | 2.640 | 3.366 | 3.327 | 3.269 | 3.308 | 3.295 | 3.296 | 3.400 |
| Antibody E | Urea (−) | 2.610 | 3.094 | 3.210 | 3.186 | 3.190 | 3.149 | 3.172 | 3.262 |
| | Urea (+) | 2.698 | 3.386 | 3.357 | 3.309 | 3.323 | 3.308 | 3.326 | 3.414 |
| Antibody F | Urea (−) | 0.031 | 0.036 | 0.077 | 0.130 | 0.140 | 0.166 | 0.183 | 0.204 |
| | Urea (+) | 0.034 | 0.174 | 0.541 | 0.657 | 0.649 | 0.669 | 0.675 | 0.693 | ing 350 μL of a blocking solution (1% BSA, 3% sucrose, PBS), the plates were left to stand at room temperature for 3 hours, and then the blocking solution was removed by suction, followed by air drying of the plates at room temperature.

(2) Test (ELISA) on Reactivity of Monoclonal Antibodies With Each Antigen

Using the six kinds of anti-HBsAg monoclonal antibodies (antibodies A to F) shown in Table 1, a test on their reactivity with the plates was carried out. Preparation of each antibody was carried out by the same method as in Patent Document 2 except that a recombinant peptide containing the epitope region of interest was used as the immunogen. Analysis of the epitope was also carried out by the same method as in Patent Document 2.

Antibodies A to F, that is, antibodies A to F prepared in (1), were diluted to 1 μg/mL with an antibody dilution liquid (0.024 M potassium dihydrogen phosphate, 0.076 M dipotassium hydrogen phosphate, 0.25 M sodium chloride, 0.02 M EDTA 2 Na. 1% polyvinylpyrrolidone (k=30), 1% BSA, 0.05% Tween 20 (trade name); pH 7.3), to prepare antibody solutions.

TABLE 1

| Antibody | Epitope |
|---|---|
| Antibody A | a-loop structure |
| Antibody B | 31-50 a.a., linear |
| Antibody C | 51-60 a.a., linear |
| Antibody D | 111-130 a.a., linear |
| Antibody E | 111-130 a.a., linear |
| Antibody F | 151-170 a.a., linear |
| Antibody G | 51-60 a.a., linear |

To the plates prepared in (1), each antibody solution was dispensed at 100 μL/well, and the plates were then left to stand at room temperature for 60 minutes. After five times of washing with a plate washing liquid (PBS containing 0.05% Tween 20 (trade name)), a labeled antibody solution (a solution prepared by 10,000-fold dilution of an HRP-labeled anti-mouse IgG antibody with the antibody dilution liquid) was dispensed at 100 μL/well, and then the plates were left to stand at room temperature for 60 minutes. After three times of washing with the plate washing liquid, a Antibody A is an antibody that recognizes the a-loop structure of HBsAg. By the reduction of the antigen, its reactivity with the antigen remarkably decreased. This was thought to be due to the fact that the spatial structure of the antigen which can be recognized by antibody A was destroyed by the reduction of the antigen. On the other hand, antibodies B, C, and F showed low reactivities with the unreduced antigen, but high reactivities with the reduced antigen. These antibodies showed even higher reactivities in the presence of urea. Antibodies D and F were found to show high reactivities with the unreduced antigen, and to show even higher reactivities with the reduced antigen. On the other hand, they were hardly influenced by urea.

Example 2

Reactivities of Autoantibody-Positive Samples With Reduced Antigen>

For eight serum samples positive for anti-HBs antibody (HBsAb), a test on the reactivity with the reduced antigen was carried out. Unreduced/reduced antigen-immobilized plates were prepared by the same method as in Example 1.

The following samples were prepared.
a) Monoclonal antibody solutions

Each of antibodies A and D was diluted to 1 μg/mL with the antibody dilution liquid, to prepare antibody solutions.
b) Autoantibody-negative sera Two autoantibody-negative sera (N1 and N2) were used.
c) Autoantibody-positive sera Eight autoantibody-positive sera (P1 to P8) were used. The antibody titer of each sample was measured using LUMIPULSE HBsAb-N (manufactured by Fujirebio Inc.). The measured value for each sample is shown in Table 3.

TABLE 3

| Sample No. | HBsAb measurement value (mIU/mL) | Sample No. | HBsAb measurement value (mIU/mL) |
|---|---|---|---|
| N1 | 0 | P7 | 424 |
| N2 | 0 | P8 | 170 |
| P1 | 2946 | P9 | 22650 |
| P2 | 2293 | P10 | 20070 |

TABLE 3-continued

| Sample No. | HBsAb measurement value (mIU/mL) | Sample No. | HBsAb measurement value (mIU/mL) |
|---|---|---|---|
| P3 | 1736 | P11 | 15460 |
| P4 | 704 | P12 | 13330 |
| P5 | 543 | P13 | 4840 |
| P6 | 501 | P14 | 1460 |

To the plates, the antibody dilution liquid was dispensed at 100 and 10 μL each of the antibody solutions and the samples were added thereto, followed by leaving the plates to stand at room temperature for 60 minutes. After five times of washing with the plate washing liquid, a labeled antibody solution (a solution prepared by 10.000-fold dilution of an HRP-labeled anti-mouse IgG antibody or an HRP-labeled anti-human IgG antibody with the antibody dilution liquid) was dispensed at 100 and then the plates were left to stand at room temperature for 60 minutes. After three times of washing with the plate washing liquid, a substrate solution (TMB solution) was dispensed at 100 μL/well, and the plates were left to stand at room temperature for 30 minutes, followed by dispensing 2 N sulfuric acid at 100 μL/well to stop the reaction. The absorbance at 450/630 nm was measured for each well. Table 4 shows the values calculated by subtracting the absorbance of the blank (PBS alone) from the absorbance for each well.

TABLE 4

| Immobilization Condition | Urea (−) | | | Urea (+) | | |
|---|---|---|---|---|---|---|
| DTT (mM): | 0 | 10 | 50 | 0 | 10 | 50 |
| Antibody A | 2.669 | −0.005 | −0.007 | 2.465 | −0.002 | −0.005 |
| Antibody D | 2.164 | 3.007 | 2.999 | 2.143 | 2.970 | 2.925 |
| N1 | 0.221 | 0.159 | 0.152 | 0.107 | 0.008 | −0.007 |
| N2 | 0.260 | 0.264 | 0.255 | 0.100 | 0.013 | 0.018 |
| P1 | 0.676 | 0.091 | 0.093 | 0.606 | 0.005 | 0.001 |
| P2 | 1.180 | 0.582 | 0.688 | 1.137 | 0.225 | 0.195 |
| P3 | 1.139 | 0.139 | 0.128 | 0.975 | 0.030 | 0.014 |
| P4 | 0.929 | 0.476 | 0.463 | 0.587 | 0.017 | 0.020 |
| P5 | 1.085 | 0.221 | 0.214 | 0.852 | 0.059 | 0.022 |
| P6 | 0.639 | 0.306 | 0.298 | 0.448 | 0.028 | 0.024 |
| P7 | 0.568 | 0.177 | 0.176 | 0.433 | 0.010 | 0.007 |
| P8 | 0.343 | 0.220 | 0.217 | 0.220 | 0.026 | 0.016 |

It was confirmed that the eight autoantibody-positive samples show decreased reactivities after the reduction of the antigen. Although two cases (P2 and P4) out of the eight cases showed weak reaction with the reduced antigen, their reactivities with the antigen denatured with the reducing agent and urea were remarkably low. On the other hand, antibody D did not show a decreased reactivity due to the reducing agent and urea, and rather showed an increased reactivity. From these results, it was suggested that, in an immunoassay of HBsAg in a serum sample, by reducing the sample and using antibody D in the antigen-antibody reaction system, reaction of the autoantibodies contained in the sample with the antigen can be decreased, to thereby increase the reactivity in the antigen-antibody reaction of interest.

Example 3

Competitive Test Between Autoantibody-Positive Samples and Anti-HBsAg Monoclonal Antibodies Whether the human anti-HBsAg antibodies contained in autoantibody-positive samples compete with the monoclonal antibodies or not was studied.

Six autoantibody-positive serum samples (P9 to P14) were used. The antibody titer of each serum sample was measured using LUMIPULSE HBsAb-N (manufactured by Fujirebio Inc.). The measured value for each sample was as shown in Table 3.

An unreduced antigen-immobilized plate was prepared by the same method as in Example 1. Each of antibodies A, D, E, and F was diluted to 100 μg/mL with the antibody dilution liquid, and dispensed at 100 μL/well. Each of serum samples P9 to P14 was 5-fold diluted with PBS, and further dispensed at 10 μL/well into the wells containing the dispensed antibodies. After leaving the plate to stand at room temperature for 60 minutes, the plate was washed five times with the plate washing liquid. A labeled antibody solution (a solution prepared by 10,000-fold dilution of an HRP-labeled anti-mouse IgG antibody or an HRP-labeled anti-human IgG antibody with the antibody dilution liquid) was dispensed at 100 μL/ell, and then the plate was left to stand at room temperature for 60 minutes. After three times of washing with the plate washing liquid, a substrate solution (TMB solution) was dispensed at 100 μL/well, and the plate was left to stand at room temperature for 30 minutes, followed by dispensing 2 N sulfuric acid at 100 μL/well to stop the reaction. The absorbance at 450/630 nm was measured for each well. Table 5 shows the values calculated by subtracting the absorbance of the blank (PBS alone) from the absorbance for each well.

TABLE 5

| Sample/Antibody | NC Absorbance | A | | D | | E | | F | |
|---|---|---|---|---|---|---|---|---|---|
| | | Absorbance | Ratio to NC (%) | Absorbance | Ratio to NC (%) | Absorbance | Ratio to NC (%) | Absorbance | Ratio to NC (%) |
| P9 | 0.337 | 0.022 | 6.4 | 0.345 | 102.4 | 0.383 | 113.8 | 0.394 | 117.1 |
| P10 | 0.982 | 0.249 | 25.4 | 0.974 | 99.2 | 0.948 | 96.6 | 1.092 | 111.2 |
| P11 | 1.963 | 0.776 | 39.5 | 1.704 | 86.8 | 1.540 | 78.5 | 1.826 | 93.0 |
| P12 | 0.675 | 0.280 | 41.4 | 0.751 | 111.2 | 0.686 | 101.6 | 0.723 | 107.1 |
| P13 | 0.415 | 0.082 | 19.8 | 0.437 | 105.3 | 0.417 | 100.4 | 0.442 | 106.4 |
| P14 | 0.247 | 0.158 | 63.8 | 0.355 | 143.7 | 0.313 | 126.7 | 0.324 | 131.0 |

In the cases where antibody A was added to each autoantibody-positive sample, the reactivity of the autoantibodies with the antigen largely decreased. However, in the cases where the antibody D, E, or F was added, no decrease in the reactivity was found, or a very limited decrease in the reactivity was found. It was suggested that the human anti-HBsAg antibodies in the samples compete with antibody A, but hardly compete with antibodies D, E, and F.

Example 4-1

Assay of HBsAg in Autoantibody-Positive Samples (Using DTT)

(1) Preparation of Model Samples of Autoantibody-Positive Samples

To each of two control serum samples negative for the autoantibodies (M3 and H3) with known HBsAg concentrations, Hebsbulin (polyethylene glycol-treated anti-HBs human immunoglobulin preparation) was added to a final concentration of 1000 mIU/mL, to prepare two autoantibody-positive model serum samples (M4 and H4).

(2) Sample Pretreatment

The four samples prepared in (1) (M3, M4, H3, and H4) were subjected to sample pretreatment. A pretreatment reagent was prepared by adding DTT to a base pretreatment reagent (2.39% NLS, 50 mM Tris; pH7.2) to a final concentration of 20 mM. After mixing 100 µL of each sample with 200 µL of each pretreatment reagent, the resulting mixture was warmed at 37° C. for 60 minutes. The mixture was diluted with 400 µL of ion-exchanged water to prepare a pretreated mixture. The same pretreatment was carried out also for three HBsAg-negative serum samples, to provide blanks.

(3) Construction of HBsAg Assay System

Magnetic particles on which antibody A, B, D, E, or F was immobilized were added to a particle dilution liquid (50 mM Tris-HCl, 1 mM EDTA 2Na, 2% BSA; pH 7.2) to 0.05%, to prepare magnetic particle liquids. Labeled antibodies, prepared by labeling of antibody A, D, E, or G with alkaline phosphatase, were diluted to 0.5 µg/mL using a labeled-body dilution liquid (100 mM MES, 1% BSA, 1 mM NaCl, 0.1 mM $ZnCl_2$; pH 6.8), to prepare labeled-body liquids. The epitope of antibody G is as shown in Table 1.

HBsAg was assayed using LUMIPULSE HBsAg-HQ (manufactured by Fujirebio Inc.) according to the method described in the manufacturer's instructions except that the magnetic particle liquids and the labeled-body liquids described above were used, and that the pretreated samples described above were used as serum samples. The resulting luminescence intensity (counts) was output. The measurement result under each condition is shown in Tables 6-1 and 6-2. The measurement results shown in Tables 6-1 and 6-2 are values obtained by subtracting the average count value for the three HBsAg-negative serum samples from the count value for M3, M4, H3, or H4 under each condition.

TABLE 6-1

| Particles | Antibody A | | Antibody B | | | | | |
|---|---|---|---|---|---|---|---|---|
| Labeled body | Antibody G | | Antibody A | | Antibody D | | Antibody E | |
| DTT | − | + | − | + | − | + | − | + |
| M3 | 15755 | 1565 | 13791 | 67 | 17643 | 51607 | 18603 | 57275 |
| M4 | 3865 | 5095 | 149 | 162 | 4509 | 33093 | 4780 | 35583 |

TABLE 6-1-continued

| Particles | Antibody A | | Antibody B | | | | | |
|---|---|---|---|---|---|---|---|---|
| Labeled body | Antibody G | | Antibody A | | Antibody D | | Antibody E | |
| DTT | − | + | − | + | − | + | − | + |
| H3 | N.D. | N.D. | 71843 | 161 | 40561 | 44597 | 36608 | 41220 |
| H4 | N.D. | N.D. | 1279 | 239 | 8075 | 26675 | 7583 | 25787 |

N.D. No data

TABLE 6-2

| Particles | Antibody D | | Antibody E | | Antibody F | | | |
|---|---|---|---|---|---|---|---|---|
| Labeled body | Antibody G | | Antibody G | | Antibody D | | Antibody E | |
| DTT | − | + | − | + | − | + | − | + |
| M3 | 9623 | 68633 | 8610 | 65685 | 14451 | 44949 | 14288 | 45577 |
| M4 | 3143 | 42808 | 3670 | 33340 | 5069 | 27827 | 5232 | 29390 |
| H3 | N.D. | N.D. | N.D. | N.D. | 43291 | 70821 | 39243 | 55757 |
| H4 | N.D. | N.D. | N.D. | N.D. | 11757 | 41007 | 10066 | 33878 |

N.D. No data

It was shown that, in cases where antibody A is used as the immobilized antibody or the labeled body, the result is strongly influenced by the autoantibodies when the reducing agent is not used in the pretreatment liquid, and, on the other hand, the count value decreases when the reducing agent is used, resulting in a decreased sensitivity as a whole.

In the cases where antibody D or antibody E was used as the immobilized antibody or the labeled body, using of the reducing agent in the pretreatment liquid caused an increase in the count value as a whole, and the degree of lowering of the luminescence intensity due to the presence of the autoantibodies decreased, showing a tendency to give count values that make Ab(+)/Ab(−) closer to 1. Similar tendencies were found also in the cases where antibody F was used as the immobilized antibody, and antibody D or antibody E was used as the labeled body.

From these results, it was suggested that, in cases where antibody D, E, or F is used, and HBsAg is assayed under conditions where the pretreatment liquid contains the reducing agent, the influence of the autoantibodies can be avoided, and HBsAg can be assayed with a higher sensitivity.

Example 4-2

Assay of HBsAg in Autoantibody-Positive Samples (Using TCEP or DEAET)

(1) Construction of HBsAg Assay System

Into a black 96-well microwell plate (F16 Maxisorp, manufactured by Thermo Fisher), PBS containing 5 µg/mL antibody B or antibody F was dispensed at 100 µL/well, and the plate was then left to stand at 4° C. overnight. After three times of washing with PBS, 350 µL of a blocking solution (1% BSA, 3% sucrose, PBS) was dispensed, and the plate was left to stand at room temperature for 3 hours. The blocking solution was removed by suction, and the plate was air-dried at room temperature to prepare an anti-HBsAg antibody-immobilized plate.

Labeled antibodies, prepared by labeling of antibody D or E with alkaline phosphatase, were diluted to 0.5 µg/mL with a labeled-body dilution liquid (100 mM MES, 1% BSA, 1 mM NaCl, 0.1 mM $ZnCl_2$; pH 6.8), to prepare labeled-body liquids.

(2) Preparation of Model Samples of Autoantibody-Positive Samples

To each of two serum samples negative for the autoantibodies (13(−) and H3) with known HBsAg concentrations, Hebsbulin was added to a final concentration of 1000 mIU/mL, to prepare two autoantibody-positive model serum samples (13(+) and H4).

(3) Sample Pretreatment

The four samples prepared in (2) (13(−), 13(+), H3, and H4) were subjected to sample pretreatment. A pretreatment reagent was prepared by adding TCEP or DEAET to a base pretreatment reagent (2.39% NLS. 50 mM Tris; pH7.2) to a final concentration of 20 mM. After mixing 100 µL of each sample with 200 µL of each pretreatment reagent, the resulting mixture was warmed at 37° C. for 60 minutes. The same pretreatment was carried out also for three HBsAg-negative serum samples, to provide blanks.

(4) HBsAg Assay

To the anti-HBsAg antibody-immobilized plate prepared in (1), a hybridization buffer (0.024 M potassium dihydrogen phosphate, 0.076 M dipotassium hydrogen phosphate, 0.25 M sodium chloride, 0.02 M EDTA 2Na, 1% polyvinylpyrrolidone (k=30), 1% BSA, 0.05% Tween 20 (trade name); pH 7.3) was dispensed at 100 µL/well. Further, the pretreated samples in (3) were dispensed at 50 µL/well. After leaving the plate to stand at room temperature for 60 minutes, the plate was washed five times with the plate washing liquid. The labeled-body liquids prepared in (1) were dispensed at 100 µL/well, and the plate was then left to stand at room temperature for 30 minutes. Alter five times of washing with the plate washing liquid, LUMIPULSE substrate liquid (manufactured by Fujirebio Inc.) was dispensed at 100 µL/well. After leaving the plate to stand at room temperature for 20 minutes, the luminescence count for each well was measured using a microplate reader. The measurement result under each condition is shown in Table 7. The results shown in Table 7 are values obtained by subtracting the average count value for the three HBsAg-negative serum samples from the count value for 13(−), 13(±), 1-13, or H4 under each condition.

TABLE 7

| Particles<br>Labeled body | Antibody B<br>Antibody E | | | Antibody F<br>Antibody D | | | Antibody F<br>Antibody E | | |
|---|---|---|---|---|---|---|---|---|---|
| Reducing agent | — | TCEP | DEAET | — | TCEP | DEAET | — | TCEP | DEAET |
| 13 (−) | 1540 | 2015 | 1985 | 90 | 4295 | 3295 | 1230 | 6410 | 5275 |
| 13 (+) | 890 | 1950 | 1400 | −25 | 3090 | 1600 | 510 | 4585 | 2950 |
| H3 | 3820 | 5000 | 4205 | 100 | 10650 | 8855 | 4550 | 14295 | 15580 |
| H4 | 1190 | 3635 | 2005 | 0 | 6325 | 4790 | 1500 | 8800 | 7625 |

As shown in Table 7, it was shown that, also in cases where TCEP or DEAET is used as the reducing agent, the measurement result becomes less susceptible to the autoantibodies when any of antibodies D, F, and F is used for the particles and/or the labeled body in the assay of HBsAg.

The invention claimed is:

1. An assay method for hepatitis B virus s antigen in a sample separated from a living body, the method comprising:
    a pretreatment step of mixing the sample with a pretreatment reagent containing a reducing agent, to reduce hepatitis B virus s antigen; and
    an immunoassay step of subjecting the pretreated sample to an immunoassay of hepatitis B virus s antigen using at least one antibody or antigen-binding fragment thereof capable of antigen-antibody reaction with a reduced peptide composed of the amino acids at positions 98 to 179 of the amino acid sequence of SEQ ID NO:1 in hepatitis B virus s antigen.

2. The method according to claim 1, wherein
    the reducing agent is at least one reducing agent selected from the group consisting of 2-(diethylamino)ethanethiol hydrochloride (DEAET), tris(2-carboxyethyl)phosphine hydrochloride (TCEP), dithiothreitol (DTT), 2-mercaptoethanol (ME), cysteamine, and tributylphosphine (TBP); and
    the final concentration of the reducing agent in the pretreatment step is 0.5 to 100 mM.

3. The method according to claim 1, wherein the antibody is capable of antigen-antibody reaction with a reduced peptide composed of the amino acids at positions 111 to 170 of the amino acid sequence of SEQ ID NO:1 in hepatitis B virus s antigen.

4. The method according to claim 3, wherein the antibody is capable of antigen-antibody reaction with a reduced peptide composed of the amino acids at positions 111 to 156 of the amino acid sequence of SEQ ID NO:1 in hepatitis B virus s antigen.

5. The method according to claim 4, wherein the antibody is capable of antigen-antibody reaction with a reduced peptide composed of the amino acids at positions 111 to 130 of the amino acid sequence of SEQ ID NO:1 in hepatitis B virus s antigen.

6. The method according to claim 1, wherein the pretreatment step is carried out under conditions at a pH of 3.0 to 12.0.

7. The method according to claim 1, wherein the pretreatment reagent further contains a surfactant.

8. An assay kit for hepatitis B virus s antigen, comprising:
    (1) a pretreatment reagent containing a reducing agent; and
    (2) an immunoassay reagent containing at least one antibody or antigen-binding fragment thereof capable of antigen-antibody reaction with a reduced peptide composed of the amino acids at positions 98 to 179 of the amino acid sequence of SEQ ID NO:1 in hepatitis B virus s antigen.

\* \* \* \* \*

SEQUENCE LISTING

<160> NUMBER OF SEQ ID NOS: 1

<210> SEQ ID NO 1
<211> LENGTH: 226
<212> TYPE: PRT
<213> ORGANISM: Hepatitis B virus

<400> SEQUENCE: 1

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ser Pro Val Cys
            35                  40                  45

Leu Gly Gln Asn Ser Gln Ser Pro Thr Ser Asn His Ser Pro Thr Ser
        50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Ile Val
                85                  90                  95

Leu Leu Asp Tyr Gln Gly Met Leu Pro Val Cys Pro Leu Ile Pro Gly
            100                 105                 110
```

```
Ser Thr Thr Thr Ser Thr Gly Pro Cys Lys Thr Cys Thr Thr Pro Ala
        115             120             125

Gln Gly Asn Ser Met Phe Pro Ser Cys Cys Cys Thr Lys Pro Thr Asp
    130             135             140

Gly Asn Cys Thr Cys Ile Pro Ile Pro Ser Ser Trp Ala Phe Ala Lys
145             150             155                         160

Tyr Leu Trp Glu Trp Ala Ser Val Arg Phe Ser Trp Leu Ser Leu Leu
            165             170             175

Val Pro Phe Val Gln Trp Phe Val Gly Leu Ser Pro Thr Val Trp Leu
            180             185             190

Ser Ala Ile Trp Met Met Trp Tyr Trp Gly Pro Ser Leu Tyr Ser Ile
        195             200             205

Val Ser Pro Phe Leu Pro Leu Leu Pro Ile Phe Phe Cys Leu Trp Val
    210             215             220

Tyr Ile
225
```